(12) United States Patent
Taff et al.

(10) Patent No.: US 9,421,384 B2
(45) Date of Patent: Aug. 23, 2016

(54) IMPLANTABLE MEDICAL DEVICE

(71) Applicant: BIOTRONIK SE & Co. KG, Berlin (DE)

(72) Inventors: Brian M. Taff, Portland, OR (US); Hannes Kraetschmer, West Linn, OR (US); Jie Lian, Beaverton, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 93 days.

(21) Appl. No.: 14/244,422

(22) Filed: Apr. 3, 2014

(65) Prior Publication Data

US 2014/0316479 A1    Oct. 23, 2014

Related U.S. Application Data

(60) Provisional application No. 61/813,188, filed on Apr. 18, 2013.

(51) Int. Cl.
| | |
|---|---|
| *A61N 1/00* | (2006.01) |
| *A61N 1/37* | (2006.01) |
| *A61N 1/375* | (2006.01) |
| *A61N 1/39* | (2006.01) |
| *A61N 1/05* | (2006.01) |
| *A61B 5/00* | (2006.01) |
| *A61N 1/08* | (2006.01) |

(52) U.S. Cl.
CPC ........... *A61N 1/3706* (2013.01); *A61B 5/6869* (2013.01); *A61B 5/6879* (2013.01); *A61B 5/6886* (2013.01); *A61N 1/0573* (2013.01); *A61N 1/3756* (2013.01); *A61N 1/3918* (2013.01); *A61B 5/6867* (2013.01); *A61B 5/6882* (2013.01); *A61B 5/6885* (2013.01); *A61N 2001/083* (2013.01)

(58) Field of Classification Search
USPC .................................................. 607/36, 127
See application file for complete search history.

(56) References Cited

U.S. PATENT DOCUMENTS

| | | | |
|---|---|---|---|
| 2002/0042632 A1 | 4/2002 | Iaizzo et al. | |
| 2006/0047333 A1* | 3/2006 | Tockman ............. | A61N 1/0587 607/127 |
| 2011/0160832 A1 | 6/2011 | Cohen | |
| 2011/0190785 A1* | 8/2011 | Gerber .................... | A61B 19/00 606/129 |
| 2012/0065529 A1 | 3/2012 | Cholette | |
| 2012/0323253 A1 | 12/2012 | Garai et al. | |

FOREIGN PATENT DOCUMENTS

WO          2012013360          2/2012

OTHER PUBLICATIONS

European Search Report and Annex to the European Search Report on European Patent Application No. EP 14 16 3658, dated Aug. 26, 2014 (7 pages).

* cited by examiner

*Primary Examiner* — Nicole F Lavert
(74) *Attorney, Agent, or Firm* — Buchanan Ingersoll & Rooney PC

(57) ABSTRACT

An implantable medical device includes an actuator and/or sensor portion to be fixed to bodily tissue by means of a fixation mechanism, to act on the tissue and/or to detect a signal from the tissue, wherein at least one detector element, preferably a plurality of detector elements, adapted for detecting the close proximity of bodily tissue, is arranged on the actuator and/or sensor portion of the device, and an output of the or each detector element being connected or connectable to a detection signal evaluation unit for deriving a fixation state verification from detection signals provided by the or each detector element.

14 Claims, 7 Drawing Sheets

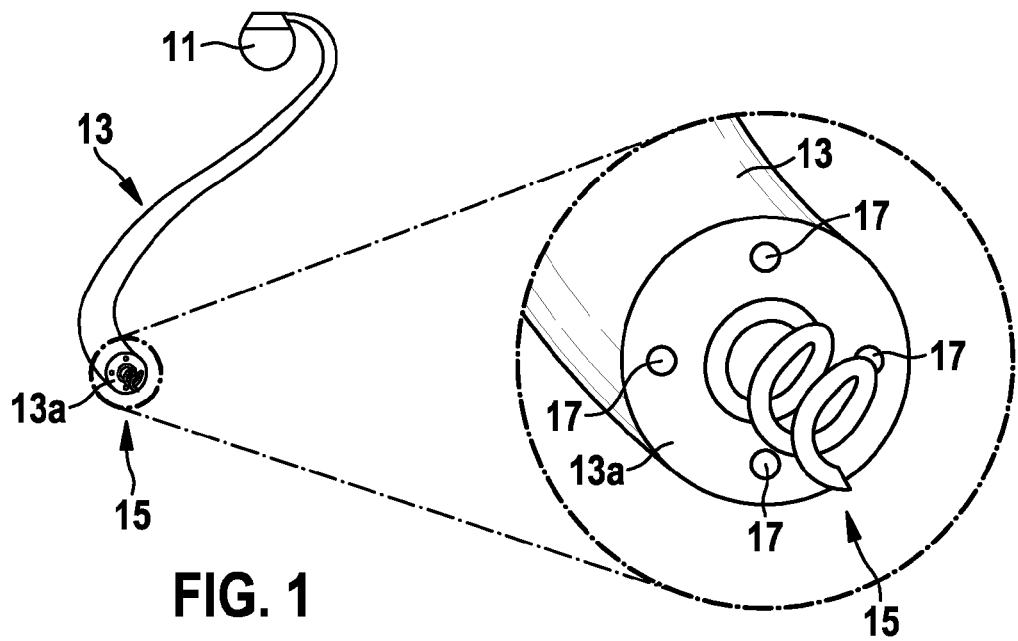
FIG. 1
FIG. 1A
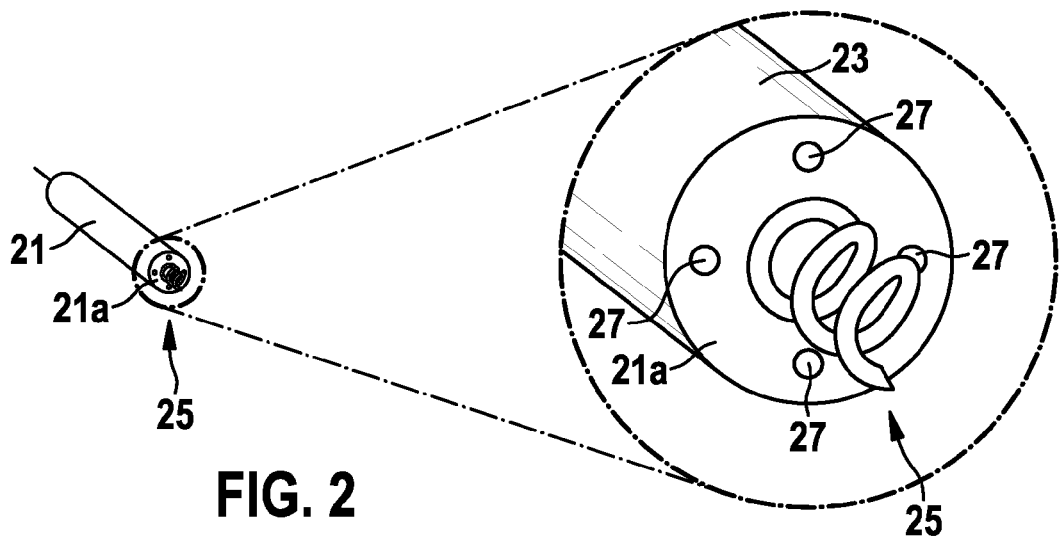
FIG. 2
FIG. 2A

IMPLANTABLE MEDICAL DEVICE

CROSS-REFERENCE TO RELATED APPLICATIONS

This patent application claims the benefit of U.S. Provisional Patent Application No. 61/813,188, filed on Apr. 18, 2013, which is hereby incorporated by reference in its entirety.

TECHNICAL FIELD

The present disclosure is related to implantable medical devices, which comprise an actuator and/or sensor portion to be fixed to bodily tissue by means of a fixation mechanism, to act on the tissue and/or to detect a signal from the tissue.

BACKGROUND

For fulfilling their functions in a reliable and durable manner, implantable medical devices like, for example, heart pacemakers or implantable cardioverters require robust contact of their respective actuator and/or sensor portions (in particular, stimulating and/or sensing electrodes) with the bodily tissue onto which they act or from which they derive sensor signals. Therefore, for decades considerable efforts have been put into developing fixation mechanisms which are both easy to operate and reliable. Nevertheless, as during the implantation of an implantable medical device there can be no absolute certainty as to the initial quality and/or durability and/or robustness, respectively, of the contact between device and tissue, it is vital to test the contact quality/durability/robustness.

For example, in commercially-deployed pacemaker lead designs, few, if any, mechanisms have been developed to offer built-in feedback/confirmation capabilities for assessing robust mechanical engagement between the lead fixation devices and the patient's myocardium. While other tangentially-leveraged strategies (see further below) have historically helped to overcome such shortcomings, recent efforts centered on the development of injectable leadless pacemaker designs present heightened needs for the prevalence of such anchoring validation schemes.

In leadless pacemakers, the delivery of pacing waveforms is weaned from the use of explicit, wired linkages to distally-stationed pulse generation units. Most proposed configurations have explored myocardial interfacing through intravenous, injectable implantation. In such systems, the devices reside within targeted heart chambers. Compared to traditional lead-reliant pacing strategies, if fixturing fails at any point, the devices are not tethered to remote units capable of providing backup anchoring. Device dislodgement in such contexts would knowingly lead to pulmonary and/or stroke complications, thus creating a greater risk to patient well-being than typical pacing approaches.

Presently, no direct method exists for assessing the effectiveness of mechanical interfacing between the lead and/or device anchors and the patient's myocardium. The dominant technique for lead-based fixation benchmarking leverages instead indirect fluoroscopy visualization techniques coupled with a withdrawal of the manipulation stylet to monitor for changes in lead tip displacement. If the withdrawal of the stylet motivates no noticeable change in the location of the lead tip, then it is assumed to have engaged with the myocardium. The efficacy of that engagement is then further validated, by checking electrical impedance readings, along with sensing and pacing thresholds. In the case of injectable leadless pacemakers, a move functionally equivalent to the withdrawal of the manipulation stylet would center on the delivery catheter releasing the device after performing an anchoring procedure.

The drawbacks associated with the stated approaches for monitoring fixation quality motivate a variety of technical support tasks. Lacking explicit mechanical interface state reporting, in general, creates a need for significant amounts of guesswork during implant in the context of both active lead placement and the installation of injectable leadless pacemaker designs. Uncertainty regarding the condition of the anchoring within the myocardium thereby unwittingly inflates the scheduled amount of time necessary for affiliated implant procedures. Part of this inflation is grounded in the diligence required to leverage impedance and sensing/capture thresholds as indirect fixture validation metrics. To properly measure such attributes of a pacing system, explicit, monitored testing procedures must occur to provide proper scrutiny of the retention response. In cases where poor fixation occurs, the lead and/or device must be repositioned and then the full sequence of electrical validation processes must be repeated until appropriate levels are reported. To complicate matters further, all of the efforts mentioned above are surrogate attempts to qualify fixation quality, and a keen risk still exists that the implanter would not realize that the device had been installed improperly. Such a condition could demand subsequent follow-up procedures that could prove even more invasive than the initial implant.

The present invention is directed toward overcoming one or more of the above-identified problems.

SUMMARY

Herein, an implantable medical device of the above-referenced type is disclosed, wherein at least one detector element, preferably a plurality of detector elements, adapted for detecting the close proximity of bodily tissue is arranged on the actuator and/or sensor portion of the device. An output of the or each detector element is connected or connectable to a detection signal evaluation unit for deriving a fixation state verification from detection signals provided by the or each detector element. The proposed solution to improved monitoring and validation of the fixation response, thus, centers on the use of one or more sensors stationed at or near the lead and/or device terminus that interfaces with the myocardium.

The present disclosure presents a proper means for assessing robust mechanical fixation and easily offsets much of the iteration involved with historical electrical validation metrics. It offers key advantages for improving both patient safety as well as the reliability of our pacing systems.

By stationing a series of sensors at the lead and/or device anchoring interface, an added level of confirmation arises for reporting the mechanical fixation response. Such a strategy presents a new safety margin that surpasses that indirectly offered through efforts to monitor in-system impedances and/or sensing/capture thresholds. Additionally, such capabilities offer new flexibilities for overcoming the risks associated with device/lead over-torquing during anchoring procedures which can lead to perforation and, in catastrophic contexts, can even core through the wall of the heart.

Moreover, the present approach provides potential for saving time at implant while simultaneously mitigating the need to manage dislodgement complications (e.g., in standard lead placements) through follow-on procedures. In the context of injectable leadless pacemakers, mechanically separating the device from the implant catheter after performing what one hopes has been a viable anchor insertion, presents a substantial patient risk for pulmonary embolism and/or stroke. With interface tracking in hand, it is possible to offset this risk and develop a key marketing and safety advantage for injectable device configurations. Conveniently, such a system offers added capabilities to our traditional lead designs potentially crafting a notable differentiator to further complement their known reliability.

In some embodiments of the present invention, the device comprises a plurality of detector elements, each being connected to an interface response detection channel within the detection signal evaluation unit. The interface response detection channels at their outputs are connected to a tissue contact assessment unit within the detection signal evaluation unit. More specifically, herein the interface response detection channels each comprise a threshold discriminator function for comparing the respective input detection signal to a predetermined threshold value. Furthermore, in such devices, in the tissue contact assessment unit a tissue contact decision algorithm for combining the output signals from the interface response section channels is implemented, to derive a decision as to whether the actuator and/or sensor portion is sufficiently fixed to the bodily tissue.

In a large variety of embodiments of the present invention, the or at least one detector element is selected from the group comprising or consisting of light emitter/photo detector elements, infrared (IR) emitter/IR detector elements, pressure detector elements, piezo elements, acoustic emitter/detector elements, strain gauge elements, and/or electrochemical impedance spectroscopy (EIS) detector elements. The sensors can, thus, be realized in a variety of ways using a number of different technologies to report the extent to which robust mechanical contact has occurred following a lead or device implant procedure. More specifically, in some multi-sensor implementations, plural sensors of the same type can be employed, whereas in other multi-sensor configurations, different sensors from the above group can be combined in a single device, to combine the specific advantages of different measuring methods with each other and to arrive at an even higher level of validity of the fixation state verification obtained from the several detection signals.

In further embodiments of the present invention, the or at least one detector element is arranged on a distal end face of the actuator and/or sensor portion. Alternatively, or even in combination with the aforementioned embodiments, the or at least one detector element can be arranged on a distal circumferential portion of the actuator and/or sensor portion.

In further embodiments, plural detector elements are arranged on the distal end face and/or the distal circumferential portion of the actuator and/or sensor portion with predetermined, preferably equal, spacings between each other. In the case where multiple sensors track the interface response, spacing them at distinct locations surrounding the terminus of the lead or device would render a means for sampling anchoring quality using a variety of points.

Such flexibility, in turn, provides a means for developing a voting algorithm that would provide enhanced resolution for screening the quality of the system's mechanical engagement with the heart tissue. While numerous voting schemes could be developed, making use of the above-mentioned plural interface response detection channels and the tissue contact assessment unit connected thereto, the simplest would likely involve either a requirement that 75% or 100% of the in-system sensors report contact validation values above a prescribed threshold. If such conditions were met, the fixation could, in turn, be graded as robust, helping to offset the chances of the anchoring system only interfacing with thin filaments within the heart or only being inserted partially into the myocardium. Thus, these embodiments of the present disclosure provide more than a mere yes/no statement regarding the tissue contact of the device, i.e., can provide a quantitative assessment of the tissue contact or fixation quality, respectively.

Additionally, an effective interface monitoring capability could aid in monitoring for anchoring over-torque conditions which would serve to prevent unnecessary proliferation of necrotic tissue and aid in avoiding heart wall perforation and/or coring conditions.

In medically and economically important embodiments, the actuator and/or sensor portion of the device is embodied as a distal end portion of a catheter or an electrode lead, respectively. In other embodiments, which in the framework of recent implantation techniques become more and more important, the actuator and/or sensor portion of the device is embodied as a distal end portion of a leadless implant. Either of these embodiments comprises a heart pacemaker or cardioverter, for applying electrical pulses to heart tissue through at least one electrode forming an actuator portion of the device.

In further embodiments of the present invention, the proposed detector element configuration(s) are combined with an active fixation mechanism, in particular, a fixation helix or fixation wires to be screwed into engagement with the bodily tissue. Alternatively, arriving at comparable advantageous effects, as with active fixation mechanisms, the present disclosure can be combined with passive fixation means, like tines or barbs or similar elements for self-anchoring an actuator and/or sensor portion in bodily tissue, e.g., the trabeculae of a mammal's heart.

Further features, aspects, objects, advantages, and possible applications of the present invention will become apparent from a study of the exemplary embodiments and examples described below, in combination with the figures, and the appended claims.

DESCRIPTION OF THE DRAWINGS

FIGS. 1 and 1A schematically illustrate a first embodiment of the present invention.

FIGS. 2 and 2A schematically illustrate a second embodiment of the present invention.

DETAILED DESCRIPTION

Figure 3A:
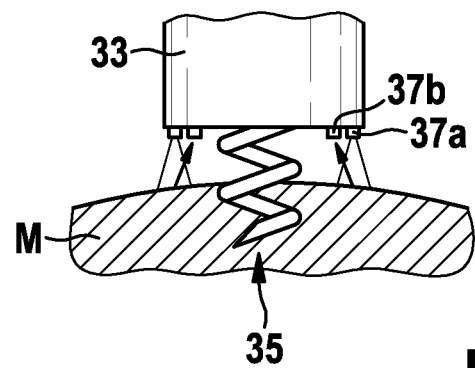
FIGS. 3A and 3B schematically illustrate a further embodiment of the present invention, i.e., an exemplary detector element configuration.

FIGS. 1 and 1A schematically illustrate an implantable heart pacemaker 11 with an implantable electrode lead 13, at the distal end of which a helically wound wire ("helix") 15 is provided as active fixation mechanism. The helix 15 can, at the same time, be connected to a pulse output of the heart pacemaker, via a conductor wire (not shown) in the electrode lead. In a distal end face 13a of the electrode lead, four detector elements 17 are arranged, spaced apart from each other by equal angular distances. The detector elements 17 serve for providing detection signals which are responsive to the proximity of bodily tissue to the end face 13a of the electrode lead 13. The number and arrangement of detector elements 17 on the distal end face 13a can take a variety of forms. The basic principles of the processing of those detection signals are explained further above; for details of an embodiment of the processing components see FIG. 10 and the corresponding part of the description, further below.

FIGS. 2 and 2A schematically illustrate a leadless pacemaker 21 which has a basically cylindrical housing with a distal end face (terminus) 21a. In the end face 21a, fully corresponding to the distal end of the electrode lead 13 in FIGS. 1 and 1A, a fixation helix 25 and four detector elements 27 are provided. As in FIGS. 1 and 1A, it is apparent for one of ordinary skill in the art that the fixation helix is just an exemplary embodiment of a large variety of fixation mechanisms which are available in the art and could be used in such implantable medical devices. Additionally, the number and arrangement of detector elements 27 on the distal end face 21a can take a variety of forms.

Figure 3B:
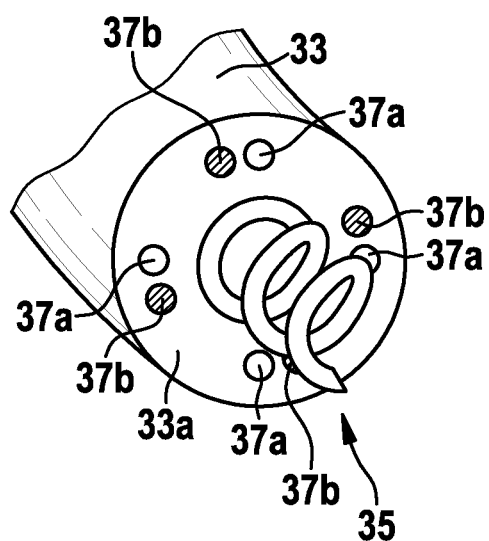

FIGS. 3A and 3B schematically illustrate a first type of detector elements which can be used in the above (or similar) medical devices, for obtaining detection signals to provide a verification or an assessment, respectively, of the fixation state of the actuator and/or sensor portion of the device with respect to adjoining bodily tissue. Again, a fixation helix 35 protruding from a distal end face 33a of an electrode lead 33 serves as an exemplary specific actuator portion, i.e., as a stimulation and/or sensing electrode. It is apparent for one of ordinary skill in the art, that at or close to the distal end of the electrode lead one or more separate electrode(s) can be provided, instead of using the helix 35 as an electrode. Likewise, it is apparent that actuators and/or sensors of a different type can be provided in/on the lead, e.g., specifically designed ablation electrodes, a laser diode or the output face of an optical waveguide, a piezo pump and/or others.

Similar as in FIG. 1A, four photo detector groups 37 are equally distributed over the end face 33a, each group consisting of an LED 37a and a photodiode 37b for receiving light of the respective LED, which is reflected back to the end face 33a from the surface of a myocardium M into which the helix 35 is screwed. Standard photo signal processing circuitry and software is provided for such sensor arrangement, for providing an adequate pre-processing of the photodiode signals with respect to reflected, scattered and absorbed light portions, indicative of the spatial position of the respective photo detector group relative to the surface of the myocardium.

Figure 4A:
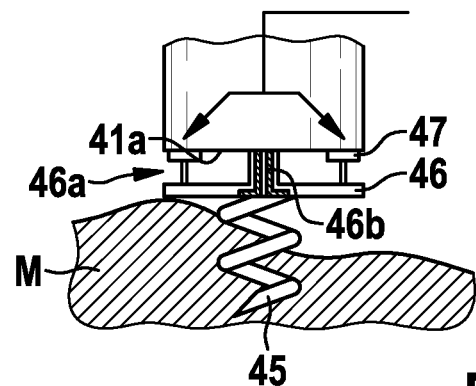
FIGS. 4A and 4B schematically illustrate a further embodiment of the present invention, i.e., another exemplary detector element configuration.
Figure 4B:
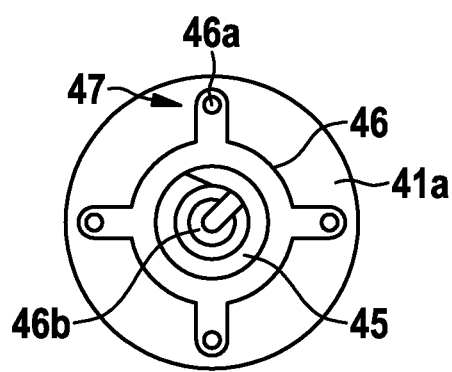

FIGS. 4A and 4B show a detector element arrangement which is similar to that of FIGS. 1A to 3B, as far as the positioning in a distal end face of the actuator/sensor portion of an implantable medical device is concerned. Therefore, in FIGS. 4A and 4B (and likewise in FIGS. 5A and 5B, 6, and 7A and 7B) reference numerals similar to those in FIGS. 1A to 3B have been designated to the several parts or portions, and a repeated explanation of the corresponding parts/portions is omitted.

The arrangement in FIGS. 4A and 4B comprises four pressure sensors 47 supporting a pressure transmission plate 46, via standoffs 46a at four equally spaced support points. In the pressure transmission plate 46, which is adapted to the shape of the helix 45, a feedthrough 46b is provided to enable a correct functioning of the helix as a fixation mechanism, without influencing the function of the detector elements. It is apparent that tissue contact of certain portions of the pressure transmission plate 46 results in the exertion of an external force on the corresponding region, which is transmitted to the closest detector element (pressure sensor) 47. Hence, a combined processing of the signals of all detector elements provides for a "mapping" of the tissue contact across the surface of the pressure transmission plate 46 and insofar of the distal end of the lead 43. It is clear that this arrangement would (as the other exemplary detector element arrangements shown in FIGS. 3A to 7B) work in an analogous manner with a leadless pacemaker, if provided at a distal end (actuator/sensor portion) thereof.

Figure 5A:
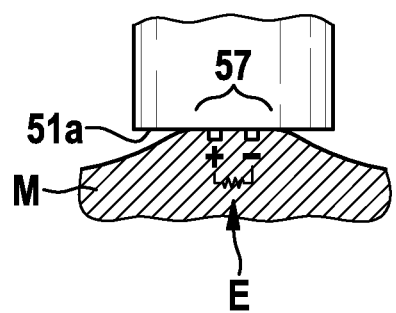
FIGS. 5A and 5B schematically illustrate a further embodiment of the present invention, i.e., another exemplary detector element configuration.
Figure 5B:
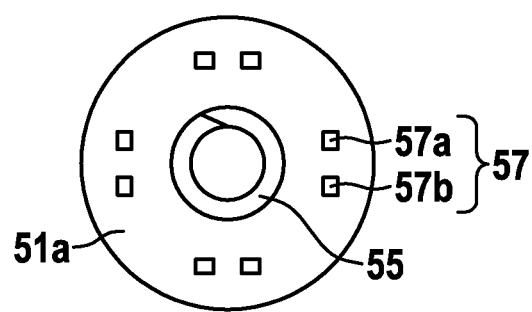

FIGS. 5A and 5B show detector elements 57 in a device end face 51a, which are of the EIS type, each comprising a pair of EIS electrodes 57a, 57b for measuring an effective impedance in the adjacent portion of the myocardial tissue between them. Basically, the sensor electrodes 57a, 57b either apply a voltage to the tissue and a resulting current is measured in an associated measurement circuit, or a current is injected into the tissue and the measurement of the resulting signal is a voltage measurement. For the sake of clarity, in FIG. 5A the helix 55 is not shown.

Figure 6:
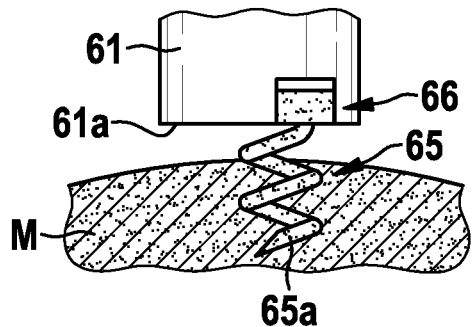
FIG. 6 schematically illustrates a further embodiment of the present invention, i.e., another exemplary detector element configuration.

FIG. 6 shows a specific embodiment of a detector arrangement implemented with piezo elements which, more generally, could be basically the same as in FIGS. 4A and 4B. In the specific embodiment of FIG. 6, in the distal end face 61a of a drug eluting device 61a piezo pump 66 is provided, which comprises a steroid reservoir 66a for storing a steroid to be slowly eluted into the myocardium M of a patient. The piezo pump 66 is in fluid connection with a lumen 65a of a hollow fixation helix 65. Deformations of the hollow helix 65 due to more or less tight tissue contact result in a transmission of corresponding forces into the piezo pump 66. These can be transformed into an electrical signal which is indicative of the tissue contact. Insofar, the piezo pump 66 or, more specifically, its piezo element in connection with an electrical signal output and signal processing (not shown), can be used as a detector element for validating tissue contact of the distal end of the device 61.

Figure 7:
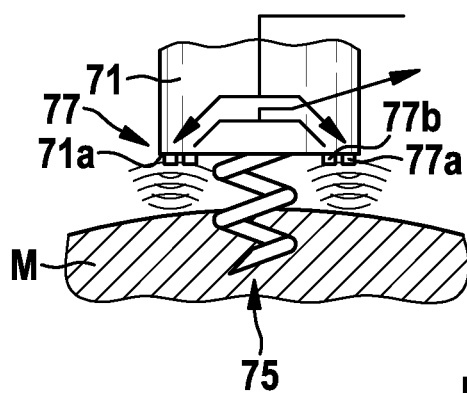
FIGS. 7 and 8 schematically illustrate further embodiments of the present invention, i.e., other exemplary detector element configurations.

FIG. 7 schematically illustrates an implementation of the present invention with acoustic sensors which are, as the detector elements of the previous embodiments, arranged in a distal end face of an implanted medical device or electrode lead or similar. In FIG. 7, that device is designated with numeral 71, and its distal end face with numeral 71a. As in previously described embodiments, a fixation helix 75 serves for holding the end of the device close to the surface of a myocardium M. Comparable to the photo detector arrangement of FIGS. 3A and 3B, the acoustic detector arrangement 77 comprises four groups of closely neighbored acoustic emitters (speakers) 77a and acoustic receivers (microphones) 77b, and tailored, commercially available signal processing provides for an adequate processing of the reflected and scattered acoustic signals, such as to derive a valid fixation state verification of the device on the myocardium therefrom.

Figure 8:
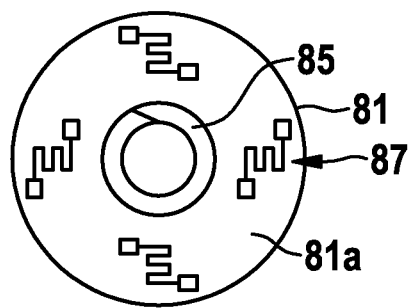

FIG. 8 is an end view of the distal end face 81a of a device 81, wherein besides a fixation helix 85, four strain gauge sensors 87 are arranged, which can be sensors of the type described in more detail under, for example, "www.omega.com" or "www.tekscan.com". The basic construction and signal processing of strain gauge sensors as such are well-known, and plural industrial applications thereof would assist one of ordinary skill in the art in implementing the method of strain gauge measurements in the framework of the present invention.

Figure 9A:
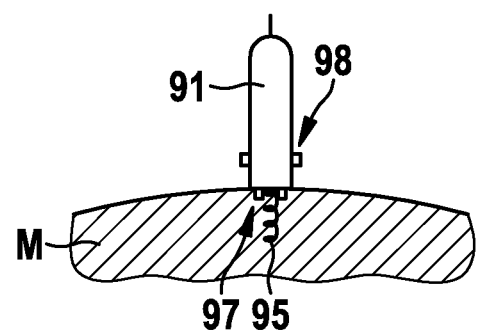
FIGS. 9A and 9B illustrate, as a further embodiment of the present invention, a leadless pacemaker in different fixation positions relative to an adjoining myocardium.
Figure 9B:
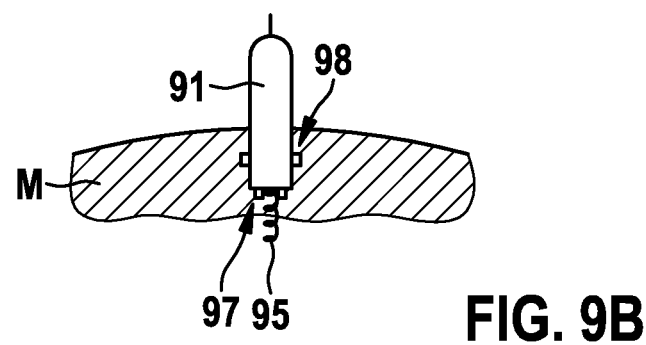

In FIGS. 9A and 9B, two positions of a leadless pacemaker 91 on the surface (FIG. 9A) or partly embedded (FIG. 9B) into a myocardium (M) are shown, for illustrating a further aspect of the present disclosure. Once again, a fixation helix 95 serves as an exemplary fixation mechanism of the pacemaker, and detector element groups 97, 98 are provided on the distal end face and on the outer circumference of the pacemaker housing, in a predefined distance from the distal end face. Although not shown, it should be understood that multiple detectors 98 can be provided on the outer circumference of the pacemaker housing that have different predefined distances to the distal end face. Whereas FIG. 9A shows a quality placement fulfilling all requirements of an adequate device function, FIG. 9B shows the result of an over-torquing of the device into the myocardium M, i.e., a perforation and/or coring response. Note that both cases could occur with implantable leads, too, and are not even restricted to configurations comprising a fixation helix. Basically, the detectors in the detector groups 97, 98 could be any of the sensors explained further above, whereas an adaptation of the processing means and algorithms for detecting a potentially dangerous over-torquing might be required. For example, in case EIS detectors or similar electrical detectors are being used, based on the detection of different impedance values by the detector groups 97 and 98, depending on whether one or both of them are embedded into the myocardium or are surrounded by blood (note that blood and myocardium have different impedance properties), and a tailored processing algorithm determining the position of the device relative to the myocardium (on or within the myocardium) can be verified, and the depth of the device embedded within the myocardium can be calculated.

Figure 10:
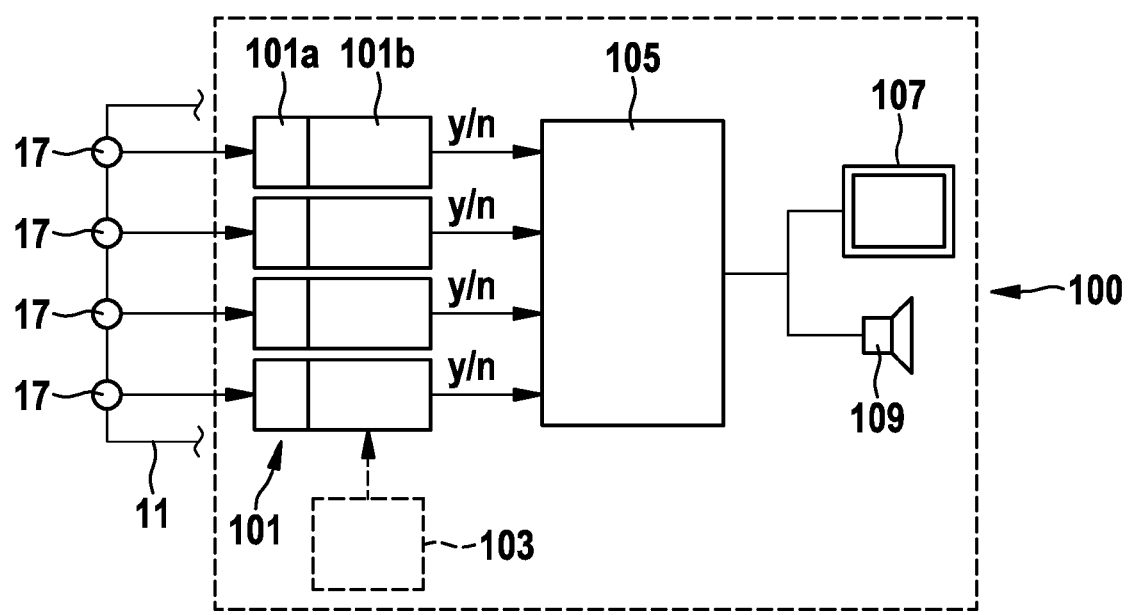
FIG. 10 is a functional block diagram schematically illustrating further aspects of the present invention.

FIG. 10 is a block diagram of essential functional blocks of an exemplary apparatus for processing signals of a plurality of detector elements for detecting the close proximity of bodily tissue to an actuator and/or sensor portion of an implanted medical device. In line with FIGS. 1A and 1B, the device is designated with numeral 11, and the detector elements are designated with numeral 17. Note that the processing apparatus (detection signal evaluation unit) 100, or major components thereof, can be implemented within the implanted device itself or in external control equipment assisting the physician in introducing and fixing the device at its site.

The apparatus 100 comprises four interface response detection channels 101, equal to the number of detector elements 17. Each of the channels 101 comprises a signal-preprocessing portion 101a, wherein detector type-dependent pre-processing, i.e., noise suppression, echo cancellation etc., is implemented. The respective pre-processed detector signals are forwarded to respective threshold discriminator portions 101b, where a comparison of the respective signal values with a threshold value is being made. The threshold value is preferably adjustable, via an optional threshold adjustment unit 103 (shown in dotted form). Hence, at the respective outputs of the interface response detection channels 101, a yes/no signal "y/n" for each of the detector elements would be available, indicating whether or not at the location of the respective detector the actuator and/or sensor portion of the device 11 is in contact with bodily tissue.

These signals are input into a tissue contact assessment unit 105, wherein a tissue contact decision algorithm for combining the output signals from the channels 101 is implemented. This algorithm can be of the type as mentioned further above in an exemplary embodiment, or be of another suitable type. Applying this algorithm to the pre-processed and threshold-discriminated detector signals, provides valid information as to whether the actuator and/or sensor portion of the device is sufficiently fixed to the bodily tissue at the site where it is to be placed. A display unit 107 and an alarming unit 109 are connected to the tissue contact assessment unit 105, to provide the physician with the required information.

Details pertinent to the present invention, materials and manufacturing techniques are within the skills of one of ordinary skill in the art. Numerous modifications of the embodiments mentioned and described above are possible, within the scope of the appending claims. As an example, the number and placement of the various detector elements can be varied to provide optimum results. Inter alia, it is worth mentioning that two general device embodiment classes could exist. One class would comprise wired connections to the detector elements dedicated for detecting the close proximity of bodily tissue to the actuator and/or sensor portion of the device (implant verification sensor) that could be severed after initial implant (thus offloading electrical support needs to the programmer). Another class would comprise devices with permanent linkages between the implant verification sensors and the in-implant electronics. Such designs could serve to enable ongoing interface assessments for performing lead dislodgement surveys, etc. throughout the life of the device.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

We claim:

1. An implantable medical device comprising:
   an actuator and/or sensor portion to be fixed to bodily tissue by means of a fixation mechanism, to act on the tissue and/or to detect a signal from the tissue; and
   a plurality of detector elements arranged on a distal end face and/or a distal circumferential portion of the actuator and/or sensor portion with predetermined spacings between each other, wherein at least one detector element is adapted for detecting close proximity of bodily tissue, wherein the at least one detector element generates detection signals transmitted to a detection signal evaluation unit for deriving a fixation state verification therefrom, and wherein the fixation state verification comprises a quantitative assessment of tissue contact or fixation quality.

2. The implantable medical device of claim 1, wherein the plurality of detector elements are connected to an interface response detection channel within the detection signal evaluation unit, and wherein the interface response detection channels at their outputs are connected to a tissue contact assessment unit within the detection signal evaluation unit.

3. The implantable medical device of claim 2, wherein the interface response detection channels each comprise a threshold discriminator function for comparing the respective input detection signal to a predetermined threshold value.

4. The implantable medical device of claim 2, wherein in the tissue contact assessment unit a tissue contact decision algorithm for combining the output signals from the interface response detection channels is implemented, to derive a decision as to whether the actuator and/or sensor portion is sufficiently fixed to the bodily tissue.

5. The implantable medical device of claim 1, wherein any one detector element is selected from the group comprising light emitter/photo detector elements, IR emitter/IR detector elements, pressure detector elements, piezo elements, acoustic emitter/detector elements, strain gauge elements, and EIS detector elements.

6. The implantable medical device of claim 1, wherein the fixation mechanism is an electrode lead and the actuator and/or sensor portion is placed within the electrode lead.

7. The implantable medical device of claim 1, wherein each detector element is arranged on an outer circumference of the implantable medical device at a predetermined distance from the distal end face of the actuator and/or sensor portion.

8. The implantable medical device of claim 2, wherein a combined processing of the detection signals provides for a mapping of the tissue contact.

9. The implantable medical device of claim 1, wherein the actuator and/or sensor portion of the device is embodied as a distal end portion of a catheter or an electrode lead, respectively.

10. The implantable medical device of claim 1, wherein the actuator and/or sensor portion of the device is embodied as a distal end portion of a leadless implant.

11. The implantable medical device of claim 1, further comprising a heart pacemaker or cardioverter, for applying electrical pulses to bodily tissue through at least one electrode forming an actuator portion of the device.

12. The implantable medical device of claim 1, wherein the fixation mechanism comprises an active fixation mechanism comprising a fixation helix or fixation wires to be screwed into engagement with the bodily tissue.

13. The implantable medical device of claim 1, wherein the at least one detector element adapted for detecting the close proximity of bodily tissue is in temporary connection to the detection signal evaluation unit during an implantation procedure.

14. The implantable medical device of claim 1, wherein the at least one detector element adapted for detecting the close proximity of bodily tissue is in permanent connection to the detection signal evaluation unit.

* * * * *